(12) United States Patent
Boussie et al.

(10) Patent No.: US 9,434,709 B2
(45) Date of Patent: *Sep. 6, 2016

(54) PRODUCTION OF ADIPIC ACID AND DERIVATIVES FROM CARBOHYDRATE-CONTAINING MATERIALS

(71) Applicant: Rennovia Inc., Santa Clara, CA (US)

(72) Inventors: Thomas R. Boussie, Menlo Park, CA (US); Eric L. Dias, Belmont, CA (US); Zachary M. Fresco, Redwood City, CA (US); Vincent J. Murphy, San Jose, CA (US); James Shoemaker, Gilroy, CA (US); Raymond Archer, San Jose, CA (US); Hong Jiang, Palo Alto, CA (US)

(73) Assignee: Rennovia Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/854,780

(22) Filed: Sep. 15, 2015

(65) Prior Publication Data

US 2016/0075676 A1     Mar. 17, 2016

Related U.S. Application Data

(60) Continuation of application No. 14/153,248, filed on Jan. 13, 2014, now Pat. No. 9,156,766, which is a division of application No. 12/814,188, filed on Jun. 11, 2010, now Pat. No. 8,669,397.

(60) Provisional application No. 61/311,190, filed on Mar. 5, 2010, provisional application No. 61/268,414, filed on Jun. 13, 2009.

(51) Int. Cl.

| C07C 51/36 | (2006.01) |
|---|---|
| C07C 51/31 | (2006.01) |
| C07D 309/30 | (2006.01) |
| B01J 23/40 | (2006.01) |
| B01J 23/44 | (2006.01) |
| B01J 23/46 | (2006.01) |
| B01J 23/52 | (2006.01) |
| B01J 23/652 | (2006.01) |
| B01J 23/656 | (2006.01) |
| B01J 23/89 | (2006.01) |
| B01J 35/00 | (2006.01) |
| B01J 37/02 | (2006.01) |
| C07C 51/235 | (2006.01) |
| C07C 51/377 | (2006.01) |
| C07C 51/41 | (2006.01) |
| C07C 209/00 | (2006.01) |
| C07C 253/00 | (2006.01) |
| C07D 201/08 | (2006.01) |
| C07D 223/10 | (2006.01) |
| C08G 63/16 | (2006.01) |

(Continued)

(52) U.S. Cl.
CPC .............. *C07D 309/30* (2013.01); *B01J 23/40* (2013.01); *B01J 23/44* (2013.01); *B01J 23/462* (2013.01); *B01J 23/464* (2013.01); *B01J 23/468* (2013.01); *B01J 23/52* (2013.01); *B01J 23/6525* (2013.01); *B01J 23/6562* (2013.01); *B01J 23/6567* (2013.01); *B01J 23/8906* (2013.01); *B01J 23/8913* (2013.01); *B01J 23/8926* (2013.01); *B01J 35/006* (2013.01); *B01J 37/0205* (2013.01); *C07C 51/235* (2013.01); *C07C 51/31* (2013.01); *C07C 51/377* (2013.01); *C07C 51/412* (2013.01); *C07C 201/08* (2013.01); *C07C 209/00* (2013.01); *C07C 253/00* (2013.01); *C07D 201/08* (2013.01); *C07D 223/10* (2013.01); *C08G 63/16* (2013.01); *C08G 69/14* (2013.01); *C08G 69/26* (2013.01); *C08G 69/36* (2013.01); *B01J 21/063* (2013.01); *B01J 21/066* (2013.01); *B01J 21/08* (2013.01); *B01J 21/16* (2013.01); *B01J 21/18* (2013.01); *C07B 2200/07* (2013.01); *Y02P 20/582* (2015.11)

(58) Field of Classification Search
None
See application file for complete search history.

(56) References Cited

U.S. PATENT DOCUMENTS

| 2,472,168 A | 6/1949 | Mehltretter et al. |
|---|---|---|
| 2,750,394 A | 6/1956 | Peniston |

(Continued)

FOREIGN PATENT DOCUMENTS

| CA | 2097812 A1 | 6/1992 |
|---|---|---|
| CN | 101134725 A | 3/2008 |

(Continued)

OTHER PUBLICATIONS

Abbadi, A., et al., "Effect of pH in the Pt-Catalyzed Oxidation of D-Glucose to D-Gluconic Acid," 1995, J. Mol. Catal. A: Chem., 97:111-118.

(Continued)

*Primary Examiner* — Sudhakar Katakam
*Assistant Examiner* — Jennifer C Sawyer
(74) *Attorney, Agent, or Firm* — Senniger Powers LLP

(57) ABSTRACT

The present invention generally relates to processes for the chemocatalytic conversion of a glucose source to an adipic acid product. The present invention includes processes for the conversion of glucose to an adipic acid product via glucaric acid or derivatives thereof. The present invention also includes processes comprising catalytic oxidation of glucose to glucaric acid or derivative thereof and processes comprising the catalytic hydrodeoxygenation of glucaric acid or derivatives thereof to an adipic acid product. The present invention also includes products produced from adipic acid product and processes for the production thereof from such adipic acid product.

39 Claims, No Drawings

(51) Int. Cl.
  *C08G 69/14* (2006.01)
  *C08G 69/26* (2006.01)
  *C08G 69/36* (2006.01)
  *C07C 201/08* (2006.01)
  *B01J 21/06* (2006.01)
  *B01J 21/08* (2006.01)
  *B01J 21/16* (2006.01)
  *B01J 21/18* (2006.01)

(56) References Cited

U.S. PATENT DOCUMENTS

| | | |
|---|---|---|
| 2,851,468 A | 9/1958 | Snyder |
| 2,917,520 A | 12/1959 | Cope |
| 2,929,823 A | 3/1960 | Garber et al. |
| 3,070,633 A | 12/1962 | Utne et al. |
| 3,083,236 A | 3/1963 | Utne et al. |
| 3,118,912 A | 1/1964 | Smith |
| 3,189,651 A | 6/1965 | Garber et al. |
| 3,225,066 A | 12/1965 | Baak |
| 3,326,944 A | 6/1967 | Baak |
| 3,483,228 A | 12/1969 | Garber et al. |
| 3,607,922 A | 9/1971 | Acres et al. |
| 3,671,566 A | 6/1972 | Decker et al. |
| 3,761,579 A | 9/1973 | Curtis, Jr. et al. |
| 3,860,626 A | 1/1975 | Putnin et al. |
| 3,873,614 A | 3/1975 | Lamberti et al. |
| 3,896,056 A | 7/1975 | Benjamin et al. |
| 3,917,707 A | 11/1975 | Williams et al. |
| 4,060,547 A | 11/1977 | Paulik et al. |
| 4,067,900 A | 1/1978 | Intilli |
| 4,078,139 A | 3/1978 | Barton et al. |
| 4,302,432 A | 11/1981 | Polichnowski |
| 4,337,202 A | 6/1982 | Hearon et al. |
| 4,339,387 A | 7/1982 | Fleche et al. |
| 4,363,815 A | 12/1982 | Yu et al. |
| 4,400,468 A | 8/1983 | Faber |
| 4,401,823 A | 8/1983 | Arena |
| 4,439,551 A | 3/1984 | Yeakey et al. |
| 4,533,743 A | 8/1985 | Medeiros et al. |
| 4,590,283 A | 5/1986 | Gaset et al. |
| 4,605,790 A | 8/1986 | Wojtkowski |
| 4,722,997 A | 2/1988 | Roerdink et al. |
| 4,740,605 A | 4/1988 | Rapp |
| 4,767,856 A | 8/1988 | Dockner et al. |
| 4,820,880 A | 4/1989 | Urbas |
| 4,833,230 A | 5/1989 | Kiely et al. |
| 4,843,173 A | 6/1989 | Saito et al. |
| 4,845,208 A | 7/1989 | Fuertes et al. |
| 4,900,407 A | 2/1990 | Saito et al. |
| 4,912,237 A | 3/1990 | Zeitsch |
| 4,971,657 A | 11/1990 | Avignon et al. |
| 4,977,283 A | 12/1990 | Leupold et al. |
| 5,071,754 A | 12/1991 | Walkup et al. |
| 5,132,452 A | 7/1992 | Deller et al. |
| 5,132,456 A | 7/1992 | King et al. |
| 5,149,680 A | 9/1992 | Kitson et al. |
| 5,196,617 A | 3/1993 | Kovenklioglu et al. |
| 5,247,012 A | 9/1993 | Vyvoda |
| 5,252,473 A | 10/1993 | Walkup et al. |
| 5,264,624 A | 11/1993 | Vogtel et al. |
| 5,276,240 A | 1/1994 | Timmons et al. |
| 5,281,647 A | 1/1994 | Eapen |
| 5,290,852 A | 3/1994 | Vyvoda |
| 5,359,137 A | 10/1994 | Burke |
| 5,426,219 A | 6/1995 | Lehnhardt et al. |
| 5,426,252 A | 6/1995 | Sherif |
| 5,430,214 A | 7/1995 | Smith et al. |
| 5,434,233 A | 7/1995 | Kiely et al. |
| 5,484,914 A | 1/1996 | Skibida et al. |
| 5,487,987 A | 1/1996 | Frost et al. |
| 5,516,960 A | 5/1996 | Robinson |
| 5,562,777 A | 10/1996 | Farone et al. |
| 5,599,977 A | 2/1997 | Kiely et al. |
| 5,616,496 A | 4/1997 | Frost et al. |
| 5,625,110 A | 4/1997 | Schoedel et al. |
| 5,683,952 A | 11/1997 | Onozawa et al. |
| 5,721,189 A | 2/1998 | Zhang |
| 5,726,046 A | 3/1998 | Farone et al. |
| 5,731,467 A | 3/1998 | Fleche |
| 5,766,439 A | 6/1998 | Eyal et al. |
| 5,772,013 A | 6/1998 | Kunz et al. |
| 5,773,677 A | 6/1998 | Lansink-Rotgerink et al. |
| 5,789,333 A | 8/1998 | Angelici et al. |
| 5,811,628 A | 9/1998 | Weber et al. |
| 5,820,687 A | 10/1998 | Farone et al. |
| 5,900,511 A | 5/1999 | Sengupta et al. |
| 5,919,994 A | 7/1999 | Rao |
| 5,922,635 A | 7/1999 | Olah et al. |
| 5,981,420 A | 11/1999 | Nakano et al. |
| 5,986,127 A | 11/1999 | Ionkin et al. |
| 5,998,657 A | 12/1999 | Gogate et al. |
| 6,008,418 A | 12/1999 | Baur et al. |
| 6,028,025 A | 2/2000 | Ying et al. |
| 6,049,004 A | 4/2000 | Kiely et al. |
| 6,087,296 A | 7/2000 | Harper |
| 6,127,585 A | 10/2000 | Duzick et al. |
| 6,147,027 A | 11/2000 | Miyake et al. |
| 6,147,208 A | 11/2000 | Achhammer et al. |
| 6,180,830 B1 | 1/2001 | Jacquot |
| 6,228,800 B1 | 5/2001 | Yamaguchi et al. |
| 6,232,264 B1 | 5/2001 | Lukehart et al. |
| 6,391,821 B1 | 5/2002 | Satoh et al. |
| 6,403,521 B1 | 6/2002 | Ishii et al. |
| 6,436,866 B1 | 8/2002 | Nishikido et al. |
| 6,441,202 B1 | 8/2002 | Lightner |
| 6,444,608 B1 | 9/2002 | Oki et al. |
| 6,462,220 B1 | 10/2002 | Luyken et al. |
| 6,476,260 B1 | 11/2002 | Herrmann et al. |
| 6,495,730 B1 | 12/2002 | Konishi et al. |
| 6,498,269 B1 | 12/2002 | Merbouh et al. |
| 6,500,649 B2 | 12/2002 | Fouache et al. |
| 6,518,440 B2 | 2/2003 | Lightner |
| 6,521,779 B1 | 2/2003 | Boschat et al. |
| 6,559,275 B2 | 5/2003 | Minami et al. |
| 6,569,670 B2 | 5/2003 | Anderson et al. |
| 6,569,802 B1 | 5/2003 | Ionkin |
| 6,692,578 B2 | 2/2004 | Schmidt et al. |
| 6,716,339 B2 | 4/2004 | Liu et al. |
| 6,743,928 B1 | 6/2004 | Zeitsch |
| 6,773,512 B2 | 8/2004 | Ennelin et al. |
| 6,894,135 B2 | 5/2005 | Kiely et al. |
| 6,894,160 B2 | 5/2005 | Capan et al. |
| 6,897,338 B2 | 5/2005 | Zhong et al. |
| 6,953,873 B2 | 10/2005 | Cortright et al. |
| 6,958,405 B2 | 10/2005 | Le-Khac et al. |
| 7,084,090 B2 | 8/2006 | Ishii et al. |
| 7,115,541 B2 | 10/2006 | Ishii et al. |
| 7,138,035 B2 | 11/2006 | Cui et al. |
| 7,161,005 B2 | 1/2007 | Schlingloff et al. |
| 7,166,743 B2 | 1/2007 | Zhong et al. |
| 7,179,366 B2 | 2/2007 | Harle et al. |
| 7,317,116 B2 | 1/2008 | Sanborn |
| 7,344,696 B2 | 3/2008 | Canos et al. |
| 7,354,743 B2 | 4/2008 | Vlasenko et al. |
| 7,364,880 B2 | 4/2008 | Ray et al. |
| 7,371,894 B2 | 5/2008 | Wonders et al. |
| 7,385,081 B1 | 6/2008 | Gong |
| 7,393,676 B2 | 7/2008 | Gokarn et al. |
| 7,399,855 B2 | 7/2008 | Frost |
| 7,411,078 B2 | 8/2008 | Miura et al. |
| 7,413,882 B2 | 8/2008 | Berka et al. |
| 7,432,382 B2 | 10/2008 | Sanborn et al. |
| 7,459,597 B2 | 12/2008 | Koivusalmi et al. |
| 7,517,675 B2 | 4/2009 | Vercauteren et al. |
| 7,572,925 B2 | 8/2009 | Dumesic et al. |
| 7,579,489 B2 | 8/2009 | Sanborn |
| 7,579,490 B2 | 8/2009 | Sanborn et al. |
| 7,582,444 B2 | 9/2009 | Hughes |
| 7,608,689 B2 | 10/2009 | Harris et al. |
| 2002/0111458 A1 | 8/2002 | Minami et al. |
| 2003/0015457 A1 | 1/2003 | Liu et al. |
| 2005/0009694 A1 | 1/2005 | Watts et al. |
| 2005/0233423 A1 | 10/2005 | Berka et al. |

(56) References Cited

U.S. PATENT DOCUMENTS

| | | |
|---|---|---|
| 2005/0272134 A1 | 12/2005 | Hughes |
| 2006/0084800 A1 | 4/2006 | Chenault |
| 2006/0084817 A1 | 4/2006 | Chenault |
| 2007/0027341 A1 | 2/2007 | Rossi et al. |
| 2007/0031918 A1 | 2/2007 | Dunson, Jr. et al. |
| 2007/0031919 A1 | 2/2007 | Dunson, Jr. et al. |
| 2007/0111294 A1 | 5/2007 | Burgard et al. |
| 2007/0166220 A1 | 7/2007 | Ceyer et al. |
| 2007/0193960 A1 | 8/2007 | Frank et al. |
| 2007/0215484 A1 | 9/2007 | Peterson et al. |
| 2007/0219397 A1 | 9/2007 | Holladay et al. |
| 2007/0287845 A1 | 12/2007 | Lilga et al. |
| 2008/0033187 A1 | 2/2008 | Zhao et al. |
| 2008/0033188 A1 | 2/2008 | Dumesic et al. |
| 2008/0033205 A1 | 2/2008 | Kiely et al. |
| 2008/0041366 A1 | 2/2008 | Wahnon |
| 2008/0096242 A1 | 4/2008 | Sanders et al. |
| 2008/0103232 A1 | 5/2008 | Lake et al. |
| 2008/0103318 A1 | 5/2008 | Lilga et al. |
| 2008/0103340 A1 | 5/2008 | Binder et al. |
| 2008/0206562 A1 | 8/2008 | Stucky et al. |
| 2008/0216391 A1 | 9/2008 | Cortright et al. |
| 2008/0293109 A1 | 11/2008 | Berka et al. |
| 2008/0300434 A1 | 12/2008 | Cortright et al. |
| 2008/0300435 A1 | 12/2008 | Cortright et al. |
| 2009/0018300 A1 | 1/2009 | Bloom et al. |
| 2009/0047719 A1 | 2/2009 | Burgard et al. |
| 2009/0131259 A1 | 5/2009 | Kiely et al. |
| 2009/0171037 A1 | 7/2009 | Aoshima et al. |
| 2009/0211942 A1 | 8/2009 | Cortright et al. |
| 2009/0215128 A1 | 8/2009 | Vlasenko et al. |
| 2009/0250653 A1 | 10/2009 | Kiely et al. |
| 2009/0255171 A1 | 10/2009 | Dumesic et al. |
| 2009/0270245 A1 | 10/2009 | Kumar et al. |
| 2009/0305364 A1 | 12/2009 | Burgard et al. |
| 2010/0113263 A1 | 5/2010 | Lee et al. |
| 2011/0144385 A1 | 6/2011 | Franke et al. |

FOREIGN PATENT DOCUMENTS

| | | |
|---|---|---|
| CN | 101486639 | 7/2009 |
| CN | 101695657 A | 4/2010 |
| DE | 19609069 A1 | 9/1997 |
| EP | 0096913 A1 | 12/1983 |
| EP | 0151498 A2 | 8/1986 |
| EP | 1728844 A1 | 12/2006 |
| EP | 2033958 A1 | 3/2009 |
| FR | 2556344 A1 | 6/1985 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| GB | 1044883 | 10/1966 |
| JP | 33-7620 | 8/1958 |
| JP | 53-144506 | 12/1978 |
| JP | 55-013243 | 1/1980 |
| JP | 59-190984 | 10/1984 |
| JP | 10-216518 | 8/1998 |
| JP | 2001-316311 A | 11/2001 |
| JP | 2002-308819 A | 10/2002 |
| JP | 2005-060447 A | 3/2005 |
| JP | 2005154302 | 6/2005 |
| JP | 2005-200321 A | 7/2005 |
| JP | 2005-232116 A | 9/2005 |
| JP | 2007-145736 A | 6/2007 |
| LV | 10857 B | 8/1996 |
| WO | 8201701 A1 | 5/1982 |
| WO | 9421690 A2 | 9/1994 |
| WO | 9507996 A1 | 3/1995 |
| WO | 9604224 A1 | 2/1996 |
| WO | 9638402 A1 | 12/1996 |
| WO | 2005003072 A1 | 1/2005 |
| WO | 2006005070 A1 | 1/2006 |
| WO | 2006100584 A2 | 9/2006 |
| WO | 2006119357 A2 | 11/2006 |
| WO | 2007075370 A2 | 7/2007 |
| WO | 2007075476 A2 | 7/2007 |
| WO | 2007089677 A2 | 8/2007 |
| WO | 2007141293 A1 | 12/2007 |
| WO | 2008021054 A2 | 2/2008 |
| WO | 2008070762 A1 | 6/2008 |
| WO | 2008109877 A1 | 9/2008 |
| WO | 2008144514 A2 | 11/2008 |

OTHER PUBLICATIONS

Abbadi, A., et al., "Highly Selective Oxidation of Aldonic Acids to 2-Keto-Aldonic Acids Over Pt—Bi and Pt—Pb Catalysts," 1995, App. Catal. A: General, 124:409-417.

Blanc, B., et al., "Starch-Derived Polyols for Polymer Technologies: Preparation by Hydrogenolysis on Metal Catalysts," Apr. 2000, Green Chemistry, pp. 89-91.

Brown, J.M., Equilibration of D-Glucaric Acid in Aqueous Solution, 2007, Thesis, University of Waikato, 191 pages.

Dirkx, J., et al., "The Oxidation of Glucose with Platinum on Carbon as Catalyst," 1981, J. Catal., 67:1-13.

Dirkx, J., et al., "The Oxidation of Gluconic Acid with Platinum on Carbon as Catalyst," 1981, J. Catal., 67:14-20.

Gehret, T. et al., "Convenient Large-Scale Synthesis of D-Glucaro-1,4:6,3-dilactone," 2009, J. Org. Chem., 74 (21), pp. 8373-8376.

Koso, S., et al., "Chemoselective Hydrogenolysis of Tetrahydrofurfuryl Alcohol to 1,5-Pentanediol," 2009, Chem. Commun., 2035-2037.

Koso, S., et al., "Promoting Effect of Mo on the Hydrogenolysis of Tetrahydrofurfuryl Alcohol to 1,5-pentanediol Over Rh/SiO2," 2009, J. Catal., 267:89-92.

Abstract of BG 100407, Episucres SA, 1997, 1 page.

Saha, B.C., "Hemicellulose Bioconversion," J. Ind. Microbiol. Biotechnol., 2003, 30:279-291.

Venema, F., et al., "Platinum-Catalyzed Oxidation of Aldopentoses to Aldaric Acids," 1992, J. Mol. Catal., 77:75-85.

Wang, T., et al., "Aqueous-Phase Aerobic Oxidation of Alcohols by Soluble Pt Nanoclusters in the Absence of Base," 2007, Chem. Commun., 4375-4377.

Wang T., et al., "Base-free Aqueous-Phase Oxidation of Non-Activated Alcohols with Molecular Oxygen on Soluble Pt Nanoparticles," 2009, Green Chem, 11:562-568.

Besson, M., et al., "Oxidation of Glucose and Gluconate on Pt, Pt Bi, and Pt Au Catalysts," 1996, Recueil des Travaux chimiques des pays-Bas, 115:217-221.

De La Motte, H., "Ueber die Einwirkung von Phosphorpentachlorid und Jodwasserstoffsaure auf Zuckersaure," 1879, Berichte Der Deutschen Chemischen Gesellschaft, 12/2:1571-1573.

Fischer, E., et al., "Ueber eine neue Pentonsaure und die zweite inactive Trioxyglutarsaure," 1891, Berichte Der Deutschen Chemischen Gesellschaft, 24/2:4216-4225.

Tiemann, F., et al., "Ueber Isozuckersaure," 1886, Berichte Der Deutschen Chemischen Gesellschaft, 19/1:1257-1281.

"Roadmap for Biomass Technologies in the United States," Dec. 2002, U.S Dept. of Energy, 48 pages.

"Top Value Added for Chemicals from Biomass—vol. 1: Results of Screening for Potential Candidates from Sugars and Synthesis Gas," 2004, Produced by PNNL, NREL and EERE, T. Werpy and G. Petersen, Eds., U.S. Dept. of Energy, 76 pages.

"Acidum Tartaricum (U.S.P.)—Tartaric Acid," 2/42010, Henriette's Herbal Homepage, www.henriettesherbal.com/eclectic/kings/acidum-tart.html, 5 pages.

International Search Report issued in PCT/US2010/038419, dated Jan. 31, 2011, 7 pages.

Written Opinion issued in PCT/US2010/038419, dated Jan. 31, 2011, 14 pages.

International Search Report issued in PCT/US2010/038422, dated Sep. 16, 2010, 6 pages.

Written Opinion issued in PCT/US2010/038422, dated Sep. 16, 2010, 11 pages.

International Search Report issued in PCT/US2010/038408, dated Feb. 2, 2011, 7 pages.

(56) References Cited

OTHER PUBLICATIONS

Written Opinion issued in PCT/US2010/038408, dated Feb. 2, 2011, 16 pages.
Casanova, O., et al., "Biomass into Chemicals: Aerobic Oxidation of 5-Hydroxymethyl-2-Furfural into 2,5-Furandicarboxylic Acid with Gold Nanoparticle Catalysts," 2009, ChemSusChem, 2:1138-1144.
Clarke, J.K.A., et al., "Preparation of Supported Platinum-Gold Catalysts and Alkane Reactions on Selected Platinum and Platinum-Gold Supported Clusters," 1984, App Catalysis, 9:85-108.
Dimitratos, N., et al., "Synergetic Effect of Platinum or Palladium on Gold Catalyst in the Selective Oxidation of D-Sorbitol," 2005, Catalysis Letters, 99:3-4:181-185.
Dirkx, J., et al., "The Preparation of D-Glucaric Acid by the Oxidation of D-Gluconic Acid Catalysed by Platinum on Carbon," 1977, Carbohydrate Research, 59:63-72.
Ibert, M., et al., "Determination of the Side-Products Formed During the Nitroxide-Mediated Bleach Oxidation of Glucose to Glucaric Acid," 2002, Carbohydrate Res, 337:1059-1063.
Lewkowski, J., "Synthesis, Chemistry and Applications of 5-Hydroxymethylfurfural and its Derivatives," 2001, Arkivoc (i):17-54.
Mallat, T., et al., "Oxidation of Alcohols with Molecular Oxygen on Solid Catalysts," 2004, Chem Rev, 104:3037-3058.
Mamman, A.S., et al. "Furfural: Hemicellulose/xylose-Derived Biochemical," 2008, Biofuels, Bioprod. Bioref., 2:438-454.
Mehltretter, C.L., et al., "Sugar Oxidation, Saccharic and Oxalic Acids by the Nitric Acid Oxidation of Dextrose," 1953, Ag and Food Chem, 1/12:779-783.
Merbouh, N., et al., "Facile Nitroxide-mediated Oxidations of D-Glucose to D-Glucaric Acid," 2001, Carbohydrate Res, 336:75-78.
Moore, J.A., et al., "An Improved Hydrogenation for the Preparation of Tetrahydrofuran cis-2,5-Dicarboxylic Acid," 1972, Organic Preparations and Procedures Int., 4/6:289-292.
Moreau, C., et al., "Recent Catalytic Advances in the Chemistry of Substituted Furans from Carbohydrates and in the Ensuing Polymers," 2004, Topics in Catalysis, 27/1-4:11-30.
Niu, W., et al., "Benzene-Free Synthesis of Adipic Acid," 2002, Biotechnol Prog, 18:201-211.
Ortiz-Soto, L.B., et al., "Structure-Sensitivity of Propylene Hydrogenation Over Cluster-Derived Bimetallic Pt—Au catalysts," 2006, Catalysis Letters, 107/1-2:13-17.
Pamuk, V., et al., "The Preparation of D-Glucaric Acid by Oxidation of Molasses in Packed Beds," 2001, J Chem Technol Biotechnol, 76:186-190.
Prati, L., et al., "Effect of Gold Addition on Pt and Pd Catalysts in Liquid Phase Oxidations," 2007, Topics in Catalysis, 44/1-2:319-324.
Röper, H., "Selective Oxidation of D-Glucose: Chiral Intermediates for Industrial Utilization," 1991, Carbohydrates As Organic Raw Materials, F.W. Lichtenhaler (Ed), Verlag Chemie, Weinheim, Germany, pp. 267-288.
Shen, Y., et al., "Efficient Synthesis of Lactic Acid by Aerobic Oxidation of Glycerol on Au—Pt/TiO2 Catalysts," 2010, Chem Eur J, 16:7368-7371.
Smits, P.C.C., et al., "The Selective Oxidation of Aldoses and Aldonic Acids to 2-Ketoaldonic Acids with Lead-Modified Platinum-on-Carbon Catalysts," 1986, Carbohydrate Res, 153:227-235.
Smits, P.C.C., et al., "Lead Modified Platinum on Carbon Caralysts for the Selective Oxidation of (2-) Hydroxycarbonic Acids, and Especially Polyhydroxycarbonic Acids to Their 2-Keto Derivatives," 1987, App Catalysis, 33:83-96.
Thaburet, J-F., et al., "Tempo-mediated Oxidation of Maltodextrins and D-Glucose: Effect of pH on the Selectivity and Sequestering Ability of the Resulting Polycarboxylates," 2001, Carbohydrate Res, 330:21-29.
Wenkin, M., et al., "Influence of Metallic Precursors on the Properties of Carbon-Supported Bismuth-Promoted Palladium Catalysts for the Selective Oxidation of Glucose to Gluconic Acid," 1996, App Catalysis A: General, 148:181-199.
Yong, G., et al., "Efficient Catalytic System for the Selective Production of 5-Hydroxymethylfurfural from Glucose and Fructose," 2008, Angew Chem Int Ed, 47:9345-9348.
Dijkgraaf, P.J.M., "Oxidation of Glucose to Glucaric Acid by Pt/C Catalysts," 1989, 105 pages, Thesis, Technische Universiteit Eindhoven.
Lichtenthaler, F.W., et al., "Carbohydrates as Green Raw Materials for the Chemical Industry," 2004 C.R. Chimie 7:65-90.
Merbouh, N., et al., "4-AcNH-Tempo-Catalyzed Oxidation of Aldoses to Aldaric Acids Using Chlorine or Bromine as Terminal Oxidants," 2002, J Carbohydrate Chem, 21/1&2: 65-77.
International Search Report issued in PCT/US2010/060143 dated Apr. 5, 2011, 6 pages.
Written Opinion issued in PCT/US2010/060143 dated Apr. 5, 2011, 9 pages.
Scifinder Search Results on "Xylaric Acid"—search conducted on Mar. 15, 2010, 11 Pages.
Gao, S., et al., "Low-Molecular-Weight and Oligomeric Components in Secondary Organic Aerosol from the Ozonolysis of Cycloalkenes and α-Pinene," 2004, J Phys Chem A, 108:10147-10164.
Guneral, F., et al., "Age-Related Reference Values for Urinary Organic Acids in a Healthy Turkish Pediatric Population," 1994, Clin Chem, 40(6):862-868.
Pankow, J.F., et al., "Modeling the Formation of Secondary Organic Aerosol. 1. Application of Theoretical Principles to Measurements Obtained in the α-Pinene/, β-Pinene/, Sabinene/, Δ3-Carene/, and Cyclohexene/Ozone Systems," 2001, Environ Sci Technol, 35:1164-1172.
Yang, L., et al., "Photooxidation of Dicarboxylic Acids-Part II: Kinetics, Intermediates and Field Observations," 2008, Atmospheric Environment, 42:868-880.
"Adipic Acid," compounds 24,052-4 and A2,635-7 in Aldrich Handbook of Fine Chemicals and Laboratory Equipment, Nederlands Edition, 2000, p. 40, Sigma-Aldrich, USA.
International Search Report issued in PCT/US2010/060147 dated Apr. 29, 2011, 4 pages.
Written Opinion issued in PCT/US2010/060147 dated Apr. 29, 2011, 10 pages.
Habrioux, A., et al., "Activity of Platinum-Gold Alloys for Glucose Electrooxidation in Biofuel Cells," 2007, J Phys Chem B, 111:10329-10333.
Kerzenmacher, S., et al., "Energy Harvesting by Implantable Abiotically Catalyzed Glucose Fuel Cells," 2008, J Power Sources, 182:1-17.
Second Written Opinion issued in PCT/US2010/060143 dated May 30, 2012, 6 pages.
Database Caplus Chemical Abstracts Service, Columbus, Ohio, US; Database Accession No. 1987:477541, Abstract of Bitsi et al., Journal of Organometallic Chemistry (1986), 310(1 ), 115-19.
Kouremenos, K.A., et al., Metabolic Profiling of Infant Urine Using Comprehensive Two-Dimensional Gas Chromatography: Application to the Diagnosis of Organic Acidurias and Biomarker Discovery, 2010, J Chromotography A, 1217:104-111.
White, J.M., et al. Opportunities for Catalysis in the 21st Century, 2002, BESAC Committee Report, 47 Pages.
Satoh, S., et al., "Electrochemical Reductive Cyclization of Dimethyl Dibromoalkanedioates," 1980, Hok Kaido Dai gaku Kogakubu KenKyu Hokoku, 102:33.
Abstract of CN 1651391 A, Univ Tianjin, 2005, 6 pages.
Jianhua Xu, "The Technological Progress and Market Analysis of Adipic Acid", Chemical Intermediate, No. 6, pp. 4-9, Jun. 30, 2006, Abstract Only, 3 pages.
Yuan Ma et al., "Comparison of Production Process of Adiponitrile", Henan Chemical Industry, vol. 24, No. 8, pp. 4-6, Dec. 31, 2007, Abstract Only, 1 page.

PRODUCTION OF ADIPIC ACID AND DERIVATIVES FROM CARBOHYDRATE-CONTAINING MATERIALS

REFERENCE TO RELATED APPLICATIONS

This application is a continuation of U.S. patent application Ser. No. 14/153,248, filed Jan. 13, 2014, now U.S. Pat. No. 9,156,766, issued Oct. 13, 2015, which is a division of U.S. patent application Ser. No. 12/814,188, filed Jun. 11, 2010, now U.S. Pat. No. 8,669,397, issued Mar. 11, 2014, and claims benefit of U.S. provisional application Ser. No. 61/268,414, filed Jun. 13, 2009, and U.S. provisional application Ser. No. 61/311,190, filed Mar. 5, 2010, the entire disclosures of which are incorporated herein by reference.

FIELD OF THE INVENTION

The present invention generally relates to processes for the chemocatalytic conversion of a glucose source to an adipic acid product. The present invention includes processes for the conversion of glucose to an adipic acid product via glucaric acid or derivatives thereof. The present invention also includes processes comprising the catalytic oxidation of glucose to glucaric acid and catalytic hydrodeoxygenation of glucaric acid or derivatives thereof to an adipic acid product. The present invention also relates to processes for the preparation of industrial chemicals such as adiponitrile, hexamethylene diamine, caprolactam, caprolactone, 1,6-hexanediol, adipate esters, polyamides (e.g., nylons) and polyesters from an adipic acid product obtained from processes which include the catalytic hydrodeoxygenation of glucaric acid or derivatives thereof.

BACKGROUND OF THE INVENTION

Crude oil is currently the source of most commodity and specialty organic chemicals. Many of these chemicals are employed in the manufacture of polymers and other materials. Examples include ethylene, propylene, styrene, bisphenol A, terephthalic acid, adipic acid, caprolactam, hexamethylene diamine, adiponitrile, caprolactone, acrylic acid, acrylonitrile, 1,6-hexanediol, 1,3-propanediol, and others. Crude oil is first refined into hydrocarbon intermediates such as ethylene, propylene, benzene, and cyclohexane. These hydrocarbon intermediates are then typically selectively oxidized using various processes to produce the desired chemical. For example, crude oil is refined into cyclohexane which is then selectively oxidized to "KA oil" which is then further oxidized for the production of adipic acid, an important industrial monomer used for the production of nylon 6,6. Many known processes are employed industrially to produce these petrochemicals from precursors found in crude oil. For example, see *Ullmann's Encyclopedia of Industrial Chemistry*, Wiley 2009 (7th edition), which is incorporated herein by reference.

For many years there has been an interest in using biorenewable materials as a feedstock to replace or supplement crude oil. See, for example, Klass, Biomass for Renewable Energy, Fuels, and Chemicals, Academic Press, 1998, which is incorporated herein by reference. Moreover, there have been efforts to produce adipic acid from renewable resources using processes involving a combination of biocatalytic and chemocatalytic processes. See, for example, "Benzene-Free Synthesis of Adipic Acid", Frost et al. Biotechnol. Prog. 2002, Vol. 18, pp. 201-211, and U.S. Pat. Nos. 4,400,468, and 5,487,987.

One of the major challenges for converting biorenewable resources such as carbohydrates (e.g. glucose derived from starch, cellulose or sucrose) to current commodity and specialty chemicals is the selective removal of oxygen atoms from the carbohydrate. Approaches are known for converting carbon-oxygen single bonds to carbon-hydrogen bonds. See, for example: U.S. Pat. No. 5,516,960; U.S. Patent App. Pub. US2007/0215484 and Japanese Patent No. 78,144,506. Each of these known approaches suffers from various limitations and we believe that, currently, none of such methods are used industrially for the manufacture of specialty or industrial chemicals.

Thus, there remains a need for new, industrially scalable methods for the selective and commercially-meaningful conversion of carbon-oxygen single bonds to carbon-hydrogen bonds, especially as applied in connection with the production of chemicals from polyhydroxyl-containing substrates (e.g., glucaric acid), and especially for the production of chemicals from polyhydroxyl-containing biorenewable materials (e.g., glucose derived from starch, cellulose or sucrose) to important chemical intermediates such as adipic acid.

SUMMARY OF THE INVENTION

Briefly, therefore, the present invention is directed to processes for preparing an adipic acid product from polyhydroxyl-containing biorenewable materials. In accordance with one embodiment, a process for producing an adipic acid product from a glucose source is provided which comprises converting by chemocatalytic means at least a portion of the glucose source to the adipic acid product.

In accordance with another embodiment, the process for preparing an adipic acid product comprises reacting, in the presence of a hydrodeoxygenation catalyst and a halogen source, a hydrodeoxygenation substrate and hydrogen to convert at least a portion of the hydrodeoxygenation substrate to an adipic acid product, wherein the hydrodeoxygenation substrate comprises a compound of formula I

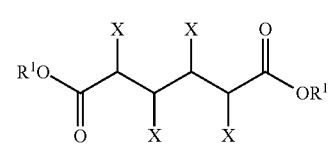

wherein X is independently hydroxyl, oxo, halo, acyloxy or hydrogen provided that at least one X is not hydrogen and $R^1$ is independently a salt-forming ion, hydrogen, hydrocarbyl, or substituted hydrocarbyl; or a mono- or di-lactone thereof.

In accordance with another embodiment, the process for preparing an adipic acid product comprises converting at least a portion of a glucose source to a hydrodeoxygenation substrate comprising glucaric acid or derivative thereof, and converting at least a portion of the glucaric acid or derivative to an adipic acid product.

The present invention is further directed to processes for preparing glucaric acid. In one embodiment, the process comprises reacting glucose with a source of oxygen in the presence of an oxidation catalyst and in the substantial absence of added base.

The present invention is further directed to processes for preparing glucaric acid by reacting glucose with oxygen in the presence of an oxidation catalyst, wherein at least a portion of the glucose is solubilized with a weak carboxylic acid, preferably acetic acid.

The present invention is further directed to processes for the preparation of industrial chemicals such as adiponitrile, hexamethylene diamine, caprolactam, caprolactone, 1,6-hexanediol, adipate esters, polyamides (e.g., nylons) and polyesters from an adipic acid product obtained from processes for the chemocatalytic conversion of a glucose source, which may include, for example, the catalytic hydrodeoxygenation of glucaric acid or derivatives thereof.

The present invention is further directed to adipic acid product, polyamides, polyesters and caprolactam produced at least in part from adipic acid product produced by the hydrodeoxygenation of a hydrodeoxygenation substrate, and, more particularly, from glucaric acid or derivative thereof.

Other objects and features will become apparent and/or will be pointed out hereinafter.

DESCRIPTION OF THE PREFERRED EMBODIMENTS

In accordance with the present invention, applicants disclose processes for the chemocatalytic conversion of a glucose source to an adipic acid product.

Further, in accordance with the present invention, applicants disclose processes for the catalytic hydrodeoxygenation of a hydrodeoxygenation substrate comprising glucaric acid and/or derivatives thereof to an adipic acid product. The catalytic hydrodeoxygenation includes reacting, in the presence of a hydrodeoxygenation catalyst (i.e., catalyst suitable for the hydrodeoxygenation reaction) and a halogen source, a hydrodeoxygenation substrate and hydrogen to convert at least a portion of the hydrodeoxygenation substrate to an adipic acid product. The hydrodeoxygenation catalyst of the present invention comprises a d-block metal (i.e., transition metal; groups 3 - 12 of the periodic table) and is hydroxyl, halo, oxo or acyloxy selective, more typically hydroxyl-selective, which increases yield and improves process economics.

The present invention also relates to processes for the catalytic production of glucaric acid from glucose. The process includes reacting glucose with oxygen in the presence of an oxidation catalyst and in the substantial absence of added base, wherein at least 50% of the glucose is converted to glucaric acid. Conducting the oxidation reaction in the substantial absence of added base facilitates product recovery and improves process economics. Further, this reaction can be conducted in the presence of a weak carboxylic acid, such as acetic acid, in which at least a portion of the glucose is solubilized. Moreover, preferred oxidation catalysts and/or oxidation reaction conditions provide yields of glucaric acid in excess of 60%, and up to 65% or more.

In another aspect of the invention, an adipic acid product prepared in accordance with the disclosed processes may be converted, according to processes known in the art, to various other industrially significant chemicals including, for example, adiponitrile, caprolactam, caprolactone, hexamethylene diamine, 1,6-hexanediol, adipate esters, polyamides (e.g., nylon) or polyesters. Thus, adiponitrile, caprolactam, caprolactone, hexamethylene diamine, 1,6-hexanediol, adipate esters, polyamides (e.g., nylon) and polyesters may be prepared from glucose derived from biorenewable sources.

I. Feedstocks

Glucose can be obtained from various carbohydrate-containing sources including conventional biorenewable sources such as corn grain (maize), wheat, potato, cassava and rice as well as alternative sources such as energy crops, plant biomass, agricultural wastes, forestry residues, sugar processing residues and plant-derived household wastes. More generally, biorenewable sources that may be used in accordance with the present invention include any renewable organic matter that includes a source of carbohydrates such as, for example, switch grass, miscanthus, trees (hardwood and softwood), vegetation, and crop residues (e.g., bagasse and corn stover). Other sources can include, for example, waste materials (e.g., spent paper, green waste, municipal waste, etc.). Carbohydrates such as glucose may be isolated from biorenewable materials using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B.V. 2007; Furia, Starch in the Food Industry, Chapter 8, *CRC Handbook of Food Additives* $2^{nd}$ Edition CRC Press, 1973. See also chapters devoted to Starch, Sugar and Syrups within *Kirk-Othmer Encyclopedia of Chemical Technology* $5^{th}$ *Edition*, John Wiley and Sons 2001. Also, processes to convert starch to glucose are known in the art, see, for example, Schenck, "Glucose and Glucose containing Syrups" in *Ullmann's Encyclopedia of Industrial Chemistry*, Wiley-VCH 2009. Furthermore, methods to convert cellulose to glucose are known in the art, see, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B.V. 2007.

II. Preparation of Glucaric Acid

In accordance with the present invention, glucose is converted to, for example, glucaric acid. The preparation of glucaric acid can be effected with glucose using oxidation methods that are generally known in the art. See, for example, U.S. Pat. No. 2,472,168, which illustrates a method for the preparation of glucaric acid from glucose using a platinum catalyst in the presence of oxygen and a base. Further examples of the preparation of glucaric acid from glucose using a platinum catalyst in the presence of oxygen and a base are illustrated in the *Journal of Catalysis* Vol. 67, p. 1-13, and p. 14-20 (1981). Other oxidation methods may also be employed, see for example, U.S. Pat. Nos. 6,049,004, 5,599,977, and 6,498,269, WO 2008/021054 and *J. Chem. Technol. Biotechnol.* Vol. 76, p. 186-190 (2001); *J. Agr. Food Chem.* Vol. 1, p.779-783 (1953); *J. Carbohydrate Chem.* Vol. 21, p. 65-77 (2002); *Carbohydrate Res.* Vol. 337, p. 1059-1063 (2002); *Carbohydrate Res.* 336, p. 75-78 (2001); *Carbohydrate Res.* Vol. 330, p. 21-29 (2001). However, these processes suffer from economic shortcomings resulting from, among other matters, process yield limitations and the requirement for additional reaction constituents.

Applicants have discovered that glucose may be converted to glucaric acid in high yield by reacting glucose with oxygen (as used herein, oxygen can be supplied to the reaction as air, oxygen-enriched air, oxygen alone, or oxygen with other constituents substantially inert to the reaction) in the presence of an oxidation catalyst and in the absence of added base according to the following reaction:

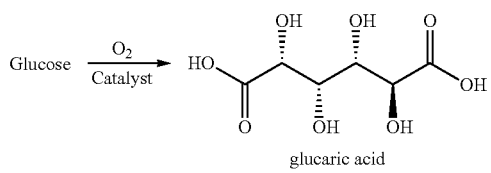 [SMILES: "O2" ; O=C(O)[C@@H](O)[C@@H](O)[C@H](O)[C@@H](O)C(=O)O]

glucaric acid

Surprisingly, conducting the oxidation reaction in the absence of added base and in accordance with the reaction conditions set forth herein, does not lead to significant catalyst poisoning effects and catalyst oxidation selectivity is maintained. In fact, catalytic selectivity can be maintained to attain glucaric acid yield in excess of 50%, even 60% and, in some instances, attain yields in excess of 65% or higher. The absence of added base advantageously facilitates separation and isolation of the glucaric acid, thereby providing a process that is more amenable to industrial application, and improves overall process economics by eliminating a reaction constituent. The "absence of added base" as used herein means that base, if present (for example, as a constituent of a feedstock), is present in a concentration which has essentially no effect on the efficacy of the reaction; i.e., the oxidation reaction is being conducted essentially free of added base. It has also been discovered that this oxidation reaction can also be conducted in the presence of a weak carboxylic acid, such as acetic acid, in which glucose is soluble. The term "weak carboxylic acid" as used herein means any unsubstituted or substituted carboxylic acid having a pKa of at least about 3.5, more preferably at least about 4.5 and, more particularly, is selected from among unsubstituted acids such as acetic acid, propionic acid or butyric acid, or mixtures thereof.

It has been further discovered that conducting the oxidation reaction under increased oxygen partial pressures and/or higher oxidation reaction mixture temperatures tends to increase the yield of glucaric acid when the reaction is conducted in the substantial absence of added base.

In these and various other embodiments, the initial pH of the reaction mixture is no greater than about 7, and typically is less than 7 such as, for example, 6 or less when a weak carboxylic acid is used to solubilize at least a portion of the glucose. In accordance with the present invention, the initial pH of the reaction mixture is the pH of the reaction mixture prior to contact with oxygen in the presence of an oxidation catalyst. It is expected that the pH of the reaction mixture after oxygen contact will vary as the reaction proceeds. It is believed that as the concentration of the glucaric acid increases (as the reaction proceeds) the pH will decrease from the initial pH.

Another advantage of the present invention is the essential absence of nitrogen as an active reaction constituent. Typically, nitrogen is employed in known processes as an oxidant such as in the form of nitrate, in many instances as nitric acid. The use of nitrogen in a form in which it is an active reaction constituent, such as nitrate or nitric acid, results in the need for $NO_x$ abatement technology and acid regeneration technology, both of which add significant cost to the production of glucaric acid from these known processes, as well as providing a corrosive environment which may deleteriously affect the equipment used to carry out the process. By contrast, for example, in the event air or oxygen-enriched air is used in the oxidation reaction of the present invention as the source of oxygen, the nitrogen is essentially an inactive or inert constituent. Thus, for example, in accordance with the present invention, an oxidation reaction employing air or oxygen-enriched air is a reaction conducted essentially free of nitrogen in a form in which it would be an active reaction constituent.

Generally, the temperature of the oxidation reaction mixture is at least about 40° C., more typically 60° C., or higher. In various embodiments, the temperature of the oxidation reaction mixture is from about 40° C. to about 150° C., from about 60° C. to about 150° C., from about 70° C. to about 150° C., from about 70° C. to about 140° C., or from about 1 kPa), at least about 25 psia (172 kPa), at least about 40 psia (276 kPa), or at least about 60 psia (414 kPa). In various embodiments, the partial pressure of oxygen is up to about 1000 psia (6895 kPa), or more typically in the range of from about 15 psia (104 kPa) to about 500 psia (3447 kPa).

The oxidation reaction is typically conducted in the presence of a solvent to glucose. Solvents suitable for the oxidation reaction include water and weak carboxylic acids such as acetic acid. Utilization of weak carboxylic acid as a solvent adds cost to the process which cost, as a practical matter, must be balanced against any benefits derived from the use thereof. Thus, suitable solvents for the present invention include water, mixtures of water and weak carboxylic acid, or weak carboxylic acid.

In general, the oxidation reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design,*

Couper et al., Elsevier 1990, which is incorporated herein by reference. It should be understood that glucose, oxygen, any solvent, and the oxidation catalyst may be introduced into a suitable reactor separately or in various combinations.

Catalysts suitable for the oxidation reaction ("oxidation catalyst") include heterogeneous catalysts, including solid-phase catalysts comprising one or more supported or unsupported metals. In various embodiments, metal is present at a surface of a support (i.e., at one or more surfaces, external or internal). Typically, metal is selected from the group consisting of palladium, platinum, and combinations thereof. Additional other metals may be present, including one or more d-block metals, alone or in combination with one or more rare earth metals (e.g. lanthanides), alone or in combination with one or more main group metals (e.g. Al, Ga, Tl, In, Sn, Pb or Bi). In general, the metals may be present in various forms (e.g., elemental, metal oxide, metal hydroxides, metal ions, etc.). Typically, the metal(s) at a surface of a support may constitute from about 0.25% to about 10%, or from about 1% to about 8%, or from about 2.5% to about 7.5% (e.g., 5%) of the total weight of the catalyst.

In various embodiments, the oxidation catalyst comprises a first metal (M1) and a second metal (M2) at a surface of a support, wherein the M1 metal is selected from the group consisting of palladium and platinum and the M2 metal is selected from the group consisting of d-block metals, rare earth metals, and main group metals, wherein the M1 metal is not the same metal as the M2 metal. In various preferred embodiments, the M1 metal is platinum and the M2 metal is selected from the group consisting of manganese, iron, and cobalt.

The M1:M2 molar ratio may vary, for example, from about 500:1 to about 1:1, from about 250:1 to about 1:1, from about 100:1 to about 1:1, from about 50:1 to about 1:1, from about 20:1 to about 1:1, or from about 10:1 to about 1:1. In various other embodiments, the M1:M2 molar ratio may vary, for example, from about 1:100 to about 1:1, from about 1:50 to about 1:1, from about 1:10 to about 1:1, from about 1:5 to about 1:1, or from about 1:2 to about 1:1.

Moreover, the weight percents of M1 and M2 relative to the catalyst weight may vary. Typically, the weight percent of M1 may range from about 0.5% to about 10%, more preferably from about 1% to about 8%, and still more preferably from about 2.5% to about 7.5% (e.g., about 5%). The weight percent of M2 may range from about 0.25% to about 10%, from about 0.5% to about 8%, or from about 0.5% to about 5%.

In various other embodiments, a third metal (M3) may be added to produce a M1/M2/M3 catalyst wherein the M3 metal is not the same metal as the M1 metal and the M2 metal. In yet other embodiments a fourth metal (M4) may be added to produce a M1/M2/M3/M4 catalyst wherein the M4 metal is not the same metal as the M1 metal, the M2 metal or the M3 metal. The M3 metal and M4 metal may each be selected from the group consisting of d-block metals, rare earth metals (e.g. lanthanides), or main group metals (e.g. Al, Ga, Tl, In, Sn, Pb or Bi).

Suitable catalyst supports include carbon, alumina, silica, ceria, titania, zirconia, niobia, zeolite, magnesia, clays, iron oxide, silicon carbide, aluminosilicates, and modifications, mixtures or combinations thereof. The preferred support materials may be modified using methods known in the art such as heat treatment, acid treatment or by the introduction of a dopant (for example, metal-doped titanias, metal-doped zirconias (e.g., tungstated-zirconia), metal-doped cerias, and metal-modified niobias). Particularly preferred supports are carbon (which may be activated carbon, carbon black, coke or charcoal), alumina, zirconia, titania, zeolite and silica. In various embodiments, the support of the oxidation catalyst is selected from the group consisting of carbon, zirconia, zeolite, and silica.

When a catalyst support is used, the metals may be deposited using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature of at least about 50° C., more typically at least about 120° C. for a period of time of at least about 1 hour, more typically 3 hours or more. In these and other embodiments, the catalyst is dried under sub-atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

The reaction product of the oxidation step will, as described above, yield glucaric acid in considerable and heretofore unexpected fraction, but may also yield derivatives thereof, such as glucarolactones. These glucarolactones, like glucaric acid, constitute hydrodeoxygenation substrate which is particularly amenable to the production of adipic acid product as hereinafter described. Glucarolactones which may be present in the reaction mixture resulting from the oxidation step include mono and di-lactones such as D-glucaro-1,4-lactone, D-glucaro-6,3- lactone, and D-glucaro-1,4:6,3-dilactone. One advantage of higher concentrations of glucarolactones is further improvement in the economics of the hydrodeoxygenation step resulting from a reduction in the amount of water produced.

Glucaric acid produced in accordance with the above may be converted to various other glucaric acid derivatives, such as salts, esters, ketones, and lactones. Methods to convert carboxylic acids to such derivatives are known in the art, see, for example, Wade, Organic Chemistry $3r^d$ ed, Prentice Hall 1995.

III. Preparation of an Adipic Acid Product

In accordance with the present invention, an adipic acid product may be prepared by chemocatalytic conversion of a glucose source. In various embodiments, preparation of an adipic acid product includes chemocatalytic conversion of a glucose source to glucaric acid. In these and other embodiments, a hydrodeoxygenation substrate comprising at least a portion of the glucaric acid or derivatives thereof is converted to an adipic acid product. Derivatives of glucaric acid include compounds as defined below.

The hydrodeoxygenation substrate comprises a compound of the formula I:

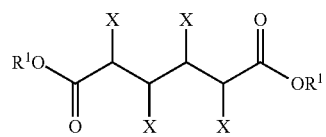

wherein X is independently hydroxyl, oxo, halo, acyloxy or hydrogen provided that at least one X is not hydrogen; $R^1$ is independently a salt-forming ion, hydrogen, hydrocarbyl, or substituted hydrocarbyl; or a mono- or di-lactone thereof.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

Salt forming ions include, without limitation, for example ammonium ions and metal ions (e.g., alkali and alkaline earth metals). When $R^1$ is a salt forming ion (i.e., a cation), the carboxyl group may be considered to be anion (i.e., carboxylate anion).

In various embodiments, the hydrodeoxygenation substrate comprises a compound of formula I, wherein X is hydroxyl and $R^1$ is independently a salt-forming ion, hydrogen, hydrocarbyl, or substituted hydrocarbyl.

As shown in formula I, the hydrodeoxygenation substrate contains a six carbon chain comprising four chiral centers. As a result several stereoisomers are possible. However, the preferred hydrodeoxygenation substrate comprises glucaric acid.

The hydrodeoxygenation substrate may also contain various ketones. For example, not wishing to be bound by theory, when glucaric acid is further oxidized, ketones such as 2-keto-glucaric acid (2,3,4-trihydroxy-5-oxohexanedioic acid) and 3-keto-glucaric acid (2,3,5-trihydroxy-4-oxo-hexanedioic acid) may be formed.

The hydrodeoxygenation substrate may comprise various lactones derived from glucaric acid. For example, not wishing to be bound by theory, it is believed that various mono- and di-lactones are present in equilibrium with glucaric acid in aqueous solution, including for example, D-glucaro-1,4-lactone, D-glucaro-6,3-lactone, and D-glucaro-1,4:6,3-dilactone. Moreover, processes have been developed to quantitatively convert glucaric acid or a salt thereof in solution to one or more lactones and recover a substantially pure lactone stream. For example see "Convenient Large-Scale Synthesis of D-Glucaro-1,4:6,3-dilactone" Gehret et al., J. Org. Chem., 74 (21), pp. 8373-8376 (2009). Also, lactones such as L-threo-4-deoxy-hex-4-enaro-6,3-lactone and L-erythro-4-deoxy-hex-4-enaro-6,3-lactone may form from the thermal decomposition of D-Glucaro-1,4:6,3-dilactone.

Therefore, in various embodiments, the hydrodeoxygenation substrate comprises D-glucaro-1,4-lactone. In these and other embodiments, the hydrodeoxygenation substrate comprises D-glucaro-6,3-lactone. Still further, in these and other embodiments, the hydrodeoxygenation substrate comprises D-glucaro-1,4:6,3-dilactone. In these and other embodiments, the hydrodeoxygenation substrate comprises L-threo-4-deoxy-hex-4-enaro-6,3-lactone. Still even further, in these and other embodiments, the hydrodeoxygenation substrate comprises L-erythro-4-deoxy-hex-4-enaro-6,3-lactone.

Also, in accordance with the present invention, an adipic acid product (formula II) may be prepared by reacting, in the presence of a hydrodeoxygenation catalyst and a halogen source, a hydrodeoxygenation substrate (formula I) and hydrogen, according to the following reaction:

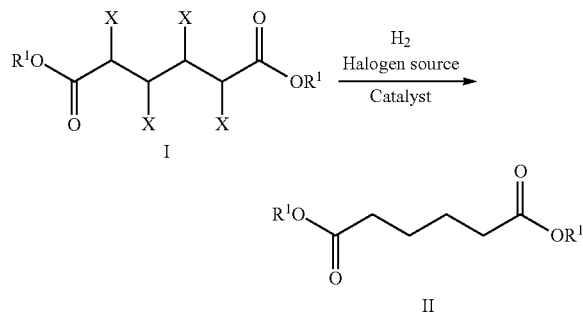

wherein X and $R^1$ are defined as described above.

In preferred embodiments, the adipic acid product (formula II) comprises adipic acid.

In the above reaction, a hydrodeoxygenation substrate is converted to an adipic acid product by catalytic hydrodeoxygenation in which carbon-hydroxyl groups are converted to carbon-hydrogen groups. In various embodiments, the catalytic hydrodeoxygenation is hydroxyl-selective wherein the reaction is completed without substantial conversion of the one or more other non-hydroxyl functional group of the substrate.

In accordance with the present invention, a hydrodeoxygenation substrate is catalytically hydrodeoxygenated in the presence of hydrogen, a halogen source and a hydrodeoxygenation catalyst. Without being bound by theory, it is believed that during this reaction the hydrodeoxygenation substrate is halogenated with the halogen source, to form a halogenated intermediate containing a carbon-halogen bond (e.g., a secondary alcohol group on the glucaric acid is converted to a halide to produce an alkyl halide). The carbon-halogen bond of the halogenated intermediate is believed to be converted to a carbon-hydrogen bond via one or more of the following pathways. In the first pathway, the halogenated intermediate reacts with hydrogen in the presence of the hydrodeoxygenation catalyst leading to the formation of a carbon-hydrogen bond along with the generation of hydrohalic acid. In the second pathway, the halogenated intermediate undergoes a dehydrohalogenation reaction to form an olefin intermediate and hydrohalic acid. The olefin is further reduced in the presence of the hydrodeoxygenation catalyst leading to the formation of a carbon-hydrogen bond (or the olefin may be an enol form of a ketone which can interconvert to a keto form which can reduce to an alcohol group which can undergo further hydrodeoxygenation). Effecting the reaction pursuant to the above described first and second pathways generates hydrohalic acid as a by-product, which is available for further reaction. In the third pathway, the halogenated intermediate reacts with hydrohalic acid leading to the formation of a carbon-hydrogen bond along with the formation of molecular halogen (or interhalogen). Effecting the reaction pursuant to the third pathway generates molecular halogen as a by-product, which is available for further reaction. One or more of the various pathways described above may occur concurrently.

It should be recognized that the hydrodeoxygenation reaction can be conducted by first forming and optionally purifying or isolating these various intermediates formed by combining a hydrodeoxygenation substrate and a halogen source and subsequently reacting the intermediate with hydrogen in the presence of the hydrodeoxygenation catalyst and optionally in the absence of any halogen source.

In various embodiments, the hydrodeoxygenation substrate is halogenated with hydrohalic acid to form a halogenated intermediate (e.g., an alkyl halide). In other embodiments, the hydrodeoxygenation substrate is halogenated with a molecular halogen to form the halogenated intermediate (e.g., an alkyl halide).

The halogen source may be in a form selected from the group consisting of atomic, ionic, molecular, and mixtures thereof. Halogen sources include hydrohalic acids (e.g., HCl, HBr, HI and mixtures thereof; preferably HBr and/or HI), halide salts, (substituted or unsubstituted) alkyl halides, or elemental halogens (e.g. chlorine, bromine, iodine or mixtures thereof preferably bromine and/or iodine). In various embodiments the halogen source is in molecular form and, more preferably, is bromine. In more preferred embodiments, the halogen source is a hydrohalic acid, in particular hydrogen bromide.

Generally, the molar ratio of halogen to the hydrodeoxygenation substrate is about equal to or less than about 1. In various embodiments, the mole ratio of halogen to the hydrodeoxygenation substrate is typically from about 1:1 to about 0.1:1, more typically from about 0.7:1 to about 0.3:1, and still more typically about 0.5:1.

Generally, the reaction allows for recovery of the halogen source and catalytic quantities (where molar ratio of halogen to the hydrodeoxygenation substrate is less than about 1) of halogen can be used, recovered and recycled for continued use as a halogen source.

Generally, the temperature of the hydrodeoxygenation reaction mixture is at least about 20° C., typically at least about 80° C., and more typically at least about 100° C. In various embodiments, the temperature of the hydrodeoxygenation reaction is conducted in the range of from about 20° C. to about 250° C., from about 80° C. to about 200° C., more preferably from about 120° C. to about 180° C., and still more preferably between about 140° C. and 180° C.

Typically, the partial pressure of hydrogen is at least about 25 psia (172 kPa), more typically at least about 200 psia (1379 kPa) or at least about 400 psia (2758 kPa). In various embodiments, the partial pressure of hydrogen is from about 25 psia (172 kPa) to about 2500 psia (17237 kPa), from about 200 psia (1379 kPa) to about 2000 psia (13790 kPa), or from about 400 psia (2758 kPa) to about 1500 psia (10343 kPa).

The hydrodeoxygenation reaction is typically conducted in the presence of a solvent. Solvents suitable for the selective hydrodeoxygenation reaction include water and carboxylic acids, amides, esters, lactones, sulfoxides, sulfones and mixtures thereof. Preferred solvents include water, mixtures of water and weak carboxylic acid, and weak carboxylic acid. A preferred weak carboxylic acid is acetic acid.

In general, the reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design,* Couper et al., Elsevier 1990, which is incorporated herein by reference. It should be understood that the hydrodeoxygenation substrate, halogen source, hydrogen, any solvent, and the hydrodeoxygenation catalyst may be introduced into a suitable reactor separately or in various combinations.

In various preferred embodiments, the hydrodeoxygenation catalyst is heterogeneous, but a suitable homogeneous catalyst may be employed. In these and various other preferred embodiments the hydrodeoxygenation catalyst comprises a solid-phase heterogeneous catalyst in which one or more metals is present at a surface of a support (i.e., at one or more surfaces, external or internal). Preferred metals are d-block metals which may be used alone, in combination with each other, in combination with one or more rare earth metals (e.g. lanthanides), and in combination with one or more main group metals (e.g., Al, Ga, Tl, In, Sn, Pb or Bi). Preferred d-block metals are selected from the group consisting of cobalt, nickel, ruthenium, rhodium, palladium, osmium, iridium, platinum and combinations thereof. More preferred d-block metals are selected from the group consisting of ruthenium, rhodium, palladium, platinum, and combinations thereof. In certain preferred embodiments, the catalyst comprises platinum. In general, the metals may be present in various forms (e.g., elemental, metal oxide, metal hydroxides, metal ions etc.). Typically, the metal(s) at a surface of a support may constitute from about 0.25% to about 10%, or from about 1% to about 8%, or from about 2.5% to about 7.5% (e.g., 5%) of the catalyst weight.

In various embodiments, the catalyst comprises two or more metals. For example, two of more metals (M1 and M2) may be co-supported on or within the same support (e.g., as a mixed-metal catalyst on silica; M1/M2/Silica catalyst), or they may be supported on different support materials. In various embodiments the hydrodeoxygenation catalyst comprises a first metal (M1) and a second metal (M2) at a surface of a support, wherein the M1 metal comprises a d-block metal and the M2 metal is selected from the group consisting of d-block metals, rare earth metals, and main group metals, wherein the M1 metal is not the same metal as the M2 metal. In various embodiments, the M1 metal is selected from the group consisting of cobalt, nickel, ruthenium, rhodium, palladium, osmium, iridium, and platinum. In more preferred embodiments, the M1 metal is selected from the group consisting of ruthenium, rhodium, palladium, and platinum. In various embodiments, the M2 metal is selected from the group consisting of titanium, vanadium, chromium, manganese, iron, cobalt, nickel, copper, molybdenum, ruthenium, rhodium, palladium, silver, tungsten, iridium, platinum, and gold. In more preferred embodiments, the M2 metal is selected from the group consisting of molybdenum, ruthenium, rhodium, palladium, iridium, platinum, and gold.

In more preferred embodiments, the M1 metal is selected from the group of platinum, rhodium and palladium, and the M2 metal is selected from the group consisting of ruthenium, rhodium, palladium, platinum, and gold. In certain more preferred embodiments, M1 is platinum and M2 is rhodium.

In various embodiments, the M1:M2 molar ratio may vary, for example, from about 500:1 to about 1:1, from about 250:1 to about 1:1, from about 100:1 to about 1:1, from about 50:1 to about 1:1, from about 20:1 to about 1:1, or from about 10:1 to about 1:1. In various other embodiments, the M1:M2 molar ratio may vary, for example, from about 1:100 to about 1:1, from about 1:50 to about 1:1, from about 1:10 to about 1:1, from about 1:5 to about 1:1, or from about 1:2 to about 1:1.

Moreover, in various embodiments, the weight percents of M1 and M2 relative to the total catalyst weight may vary. Typically, the weight percent of M1 may range from about 0.5% to about 10%, more preferably from about 1% to about 8%, and still more preferably from about 2.5% to about 7.5% (e.g., about 5%). The weight percent of M2 may range from about 0.25% to about 10%, from about 0.5% to about 8%, or from about 0.5% to about 5%.

In various other embodiments, a third metal (M3) may be added to produce a M1/M2/M3 catalyst wherein the M3 metal is not the same metal as the M1 metal and the M2 metal. In other embodiments a fourth metal (M4) may be added to produce a M1/M2/M3/M4 catalyst wherein the M4 metal is not the same metal as the M1 metal, the M2 metal or the M3 metal. M3 and M4 may each be selected from the group consisting of d-block metals, rare earth metals (e.g. lanthanides), or main group metals (e.g. Al, Ga, Tl, In, Sn, Pb or Bi).

Preferred catalyst supports include carbon, alumina, silica, ceria, titania, zirconia, niobia, zeolite, magnesia, clays, iron oxide, silicon carbide, aluminosilicates, and modifications, mixtures or combinations thereof. The preferred supports may be modified through methods known in the art such as heat treatment, acid treatment, the introduction of a dopant (for example, metal-doped titanias, metal-doped zirconias (e.g. tungstated zirconia), metal-doped cerias, and metal-modified niobias). In various preferred embodiments, the hydrodeoxygenation catalyst support is selected from the group consisting of silica, zirconia and titania. In certain preferred embodiments, a catalyst comprising platinum and rhodium is on a support comprising silica.

When a catalyst support is used, the metals may be deposited using procedures known in the art including, but not limited to incipient wetness, ion-exchange, deposition-precipitation and vacuum impregnation. When the two or more metals are deposited on the same support, they may be deposited sequentially, or simultaneously. In various embodiments, following metal deposition, the catalyst is dried at a temperature of at least about 50° C., more typically at least about 120° C. or more for a period of time of at least about 1 hour, more typically at least about 3 hours or more. In these and other embodiments, the catalyst is dried under sub-atmospheric conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of at least about 500° C. for a period of time (e.g., at least about 3 hours).

Without being bound by theory not expressly recited in the claims, catalysts mixtures (co-catalysts or mixed metal catalysts) containing more than one metal may affect separate steps of the mechanistic reaction pathway.

An adipic acid product may be recovered from the hydrodeoxygenation reaction mixture by one or more conventional methods known in the art including, for example, solvent extraction, crystallization or evaporative processes.

IV. Downstream Chemical Products

Various methods are known in the art for conversion of adipic acid to downstream chemical products or intermediates including adipate esters, polyesters, adiponitrile, hexamethylene diamine (HMDA), caprolactam, caprolactone, 1,6-hexanediol, aminocaproic acid, and polyamide such as nylons. For conversions from adipic acid, see for example, without limitation, U.S. Pat. Nos. 3,671,566, 3,917,707, 4,767,856, 5,900,511, 5,986,127, 6,008,418, 6,087,296, 6,147,208, 6,462,220, 6,521,779, 6,569,802, and Musser, "Adipic Acid" in *Ullmann's Encyclopedia of Industrial Chemistry*, Wiley-VCH, Weinheim, 2005.

In various embodiments, an adipic acid product is converted to adiponitrile wherein the adipic acid product is prepared in accordance with the present invention. Adiponitrile can be used industrially for the manufacture of hexamethylene diamine, see Smiley, "Hexamethylenediamine" in *Ullman's Encyclopedia of Industrial Chemistry*, Wiley-VCH 2009. Therefore, in further embodiments, an adipic acid product is converted to hexamethylene diamine wherein the adipic acid product is prepared in accordance with the present invention.

Adipic acid is useful in the production of polyamides, such as nylon 6,6 and nylon 4,6. See, for example, U.S. Pat. No. 4,722,997, and Musser, "Adipic Acid" in *Ullmann's Encyclopedia of Industrial Chemistry*, Wiley-VCH, Weinheim, 2005. The hexamethylene diamine formed from an adipic acid product prepared in accordance with the present invention can likewise be further used for the preparation of polyamides such as nylon 6,6 and nylon 6,12. See, for example Kohan, Mestemacher, Pagilagan, Redmond, "Polyamides" in *Ullmann's Encyclopedia of Industrial Chemistry*, Wiley-VCH, Weinheim, 2005.

Accordingly, adipic acid and a polymer precursor derived from an adipic acid product (e.g., hexamethylene diamine) may be reacted to produce a polyamide, wherein the adipic acid product is prepared in accordance with the present invention. Polymer precursor, as used herein, refers to a monomer which can be converted to a polymer (or copolymer) under appropriate polymerization conditions. In various embodiments, the polyamide comprises nylon 6,6. In these embodiments, nylon 6,6 is produced by reacting an adipic acid product with a polymer precursor derived from an adipic acid product, wherein the polymer precursor comprises hexamethylene diamine. In these embodiments, hexamethylene diamine may be prepared by converting an adipic acid product to adiponitrile which then may be converted to hexamethylene diamine, wherein the adipic acid product is prepared in accordance with the present invention.

In other embodiments, an adipic acid product is converted to caprolactam wherein the adipic acid product is prepared in accordance with the present invention. The caprolactam formed can be further used for the preparation of polyamides by means generally known in the art. Specifically, caprolactam can be further used for the preparation of nylon 6. See, for example Kohan, Mestemacher, Pagilagan, Redmond, "Polyamides" in *Ullmann's Encyclopedia of Industrial Chemistry*, Wiley-VCH, Weinheim, 2005.

In various embodiments, nylon 6 is produced by reacting caprolactam derived from an adipic acid product prepared in accordance with the present invention.

In other embodiments, adipic acid and a polymer precursor may be reacted to produce a polyester, wherein the adipic acid product is prepared in accordance with the present invention.

In other embodiments, an adipic acid product is converted to 1,6-hexanediol wherein the adipic acid product is prepared in accordance with the present invention. 1,6-hexanediol is a valuable chemical intermediate used in the production of polyesters and polyurethanes. Accordingly, in various embodiments, polyester may be prepared by reacting adipic acid and 1,6-hexandiol derived from an adipic acid product, prepared in accordance with the present invention.

In various embodiments a salt of adipic acid may be produce wherein the process comprises reacting adipic acid with hexamethylene diamine, thereby forming the salt, wherein adipic acid is prepared in accordance with the present invention.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Reactions were conducted in 1 mL glass vials housed in a pressurized vessel in accordance with the procedures described in the examples below. Product yields were determined using a Dionex ICS-3000 Chromatography system. For Example 1, the products were first separated on an Ionpac° AS 11-HC column and then quantified by conductivity detection through comparison with calibration standards. For Example 2, the products were first separated on an Acclaim° Organic Acid column and then quantified by a UV detector through comparison with calibration standards.

Example 1

Glucose To Glucaric Acid

Several catalysts were obtained from commercial vendors: Johnson Matthey 5% Pt/C (three examples; JM-23 [B103032-5, Lot #C-9090]; JM-25 [B103014-5, Lot

C9230]; and JM-27 [B-501032-5, Lot #C-9188]), Johnson Matthey 5% Pt/Al$_2$O$_3$ (two examples; JM-32 [B301013-5, Lot #C8959] and JM-33 [B301099-5, Lot #C9218]), and BASF Escat 2351 5% Pt/SiO$_2$ [Lot #A4048107]; and 1.5% Au/TiO$_2$ [Süd Chemie 02-10]. Other catalysts were prepared in accordance with the procedure described herein.

Preparation of Supported Platinum Catalysts

Multiple portions of suitably concentrated aqueous Pt(NO$_3$)$_2$ solutions (Heraeus) were added to the appropriate support (wherein the total combined volume of the Pt(NO$_3$)$_2$ solutions was matched to equal to the pore volume of the chosen support) with agitation between additions. Post impregnation, the product was dried in a furnace at 120 ° C. for 12 hours, Material for catalyst testing was prepared by reduction under flowing 5 vol. % H$_2$ in N$_2$ for 3 hours at either 200 ° C. or 350 ° C. Note that this procedure was used for all supports except carbon. See the later description for the preparation of a Pt/Carbon catalyst.

Preparation of Pt/M2/Support Catalysts (M2=Mn, Co, Fe, Re, Cu)

Approximately 7-8 mg of dried supported platinum catalyst (taken post drying but prior to reduction) was dispensed into an 8×12 array containing 1 mL glass vials. To select vials within the array, 6-7 µl (where the total addition volume was matched to equal to the pore volume of the support weighed into the vial) of suitably concentrated M2 stock solutions were added (M2=Mn, Fe, Co, Re, Cu obtained from Strem or Sigma-Aldrich, see Table 1). Post M2 addition, the mixtures were agitated via a multi-tube vortexer to impregnate the supports. Post impregnation, the glass vial arrays of Pt/M2/Support catalysts were dried in a furnace at 120° C. for 1 hour, followed by calcination at 500° C. for 3 hours followed by reduction under flowing 5 vol. % H$_2$ in N$_2$ at either 200° C. or 350° C. for 3 hours. Note that this procedure was used to prepare all Pt/M2/Support catalysts with the exception of the 1.5% Pt/1.5% Au/Titania catalyst. In this case Pt(NO$_3$)$_2$ solution was added to a dried sample of the commercial 1.5% Au/Titania catalyst [Süd Chemie 02-10] (wherein the total volume of the Pt(NO$_3$)$_2$ volume was matched to equal to the pore volume of the catalyst) with agitation, whereupon the material was dried in a furnace at 120° C. for 1 hour, followed by reduction under flowing 5 vol. % H$_2$ in N$_2$ at 350° C. for 3 hours.

Preparation of 4 wt. % Pt/Carbon Catalyst

Multiple portions of suitably concentrated aqueous Pt(NO$_3$)$_2$ solution (Heraeus) were added to 2 g of dried Degussa HP-160 furnace black carbon (3.94 mL total addition volume) with agitation between additions. Post impregnation, the 4 wt. % Pt/Carbon was dried under vacuum for one hour at 50° C., followed by reduction under flowing 5 vol. % H$_2$ in N$_2$ for three hours at 350° C.

Glucose to Glucaric Acid Reactions

Catalysts were dispensed into 1 mL vials within a 96-well reactor insert (Symyx Solutions). The reaction substrate was D-glucose (Sigma-Aldrich, 0.552M in water). To each vial was added 250 µL of glucose solution. The vials were each covered with a Teflon pin-hole sheet, a silicone pin-hole mat and steel gas diffusion plate (Symyx Solutions). The reactor insert was placed in a pressure vessel and charged three times with oxygen to 100 psig with venting after each pressurization step. The reactor was then charged to 75 psig with oxygen, or to 500 psig with air, closed and placed on a shaker, heated at the designated temperature for the specified reaction time. After the reaction time had elapsed shaking was stopped and the reactor cooled to room temperature whereupon the reactors were vented. Samples for ion-chromatography (IC) analysis were prepared by adding to each reaction vial 750 µL of a 1.067 wt. % citric acid solution (as internal standard) then the plate was covered and mixed followed by centrifugation to separate catalyst particles. Each reaction sample was further diluted by performing two 20-fold dilutions then analyzed by Ion Chromatography. In some instances, HCl was used as alternative internal standard through the addition of 100 µL of 50 ppm solution during the second 20-fold dilution. The results are presented in Table 1.

TABLE 1

| | Catalyst (wt. % M2 wt. % Pt/Support) | M1 Precursor | M2 Precursor | Temp. (° C.) | Time (Hours) | Catalyst Amount (mg) | Glucaric Acid Yield (%) |
|---|---|---|---|---|---|---|---|
| 1 | 0.06% Mn 4% Pt/Silica Davisil 635 | Pt(NO$_3$)$_2$ | Mn(NO$_3$)$_2$ | 80 | 5 | 7 | 38 |
| 2 | 0.06% Fe 4% Pt/Silica Davisil 635 | Pt(NO$_3$)$_2$ | Fe(NO$_3$)$_3$ | 80 | 5 | 8 | 28 |
| 3 | 0.06% Co 4% Pt/Silica Davisil 635 | Pt(NO$_3$)$_2$ | Co(NO$_3$)$_2$ | 80 | 5 | 8 | 34 |
| 4 | 4% Pt/Silica Davisil 635 | Pt(NO$_3$)$_2$ | None | 80 | 5 | 8 | 34 |
| 5 | 4% Pt/Silica 5 µm Cariact | Pt(NO$_3$)$_2$ | None | 90 | 5 | 8 | 50 |
| 6 | 4% Pt/Silica 5 µm Cariact | Pt(NO$_3$)$_2$ | None | 90 | 8 | 8 | 66 |
| 7 | 4% Pt/Silica Merck 10180 | Pt(NO$_3$)$_2$ | None | 90 | 5 | 8 | 40 |
| 8 | 1.91% Re 4% Pt/Silica Merck 10180 | Pt(NO$_3$)$_2$ | HReO$_4$ | 90 | 5 | 8 | 39 |
| 9 | 0.65% Cu 4% Pt/Silica Merck 10180 | Pt(NO$_3$)$_2$ | Cu(NO$_3$)$_2$ | 90 | 5 | 8 | 39 |
| 10 | 0.10% Mo 4% Pt/Silica Merck 10180 | Pt(NO$_3$)$_2$ | (NH$_4$)$_6$Mo$_7$O$_{24}$ | 90 | 5 | 8 | 38 |
| 11 | 4% Pt/Carbon Degussa HP-160 | Pt(NO$_3$)$_2$ | None | 80 | 5 | 8 | 53 |
| 12 | 4% Pt/Carbon Degussa HP-160 | Pt(NO$_3$)$_2$ | None | 90 | 8 | 8 | 60 |
| 13 | 5% Pt/C [JM-23] | | None | 80 | 5 | 10 | 52 |
| 14 | 5% Pt/C [JM-25] | | None | 80 | 5 | 10 | 57 |
| 15 | 5% Pt/C [JM-27] | | None | 80 | 5 | 10 | 57 |
| 16 | 5% Pt/Al$_2$O$_3$ [JM-32] | | None | 80 | 5 | 10 | 23 |
| 17 | 5% Pt/Al$_2$O$_3$ [JM-33] | | None | 80 | 5 | 10 | 31 |
| 18 | 5% Pt/SiO$_2$ [BASF Escat 2351] | Pt(NO$_3$)$_2$ | None | 80 | 5 | 10 | 15 |
| 19 | 8% Pt/Zirconia Daiichi Kigenso Z-1044 | Pt(NO$_3$)$_2$ | None | 90 | 5 | 8 | 52 |
| 20 | 8% Pt/Zirconia Daiichi Kigenso Z-1628 | Pt(NO$_3$)$_2$ | None | 90 | 5 | 8 | 59 |
| 21 | 8% Pt/Zirconia Ceria Daiichi Kigenso Z-1006 | Pt(NO$_3$)$_2$ | None | 90 | 5 | 8 | 54 |
| 22 | 8% Pt/Ceria Daiichi Kigenso Z-1627 | Pt(NO$_3$)$_2$ | None | 90 | 5 | 8 | 17 |
| [b]23 | [a]4% Pt/Zeolite Zeolyst CP 811C-300 | Pt(NO$_3$)$_2$ | None | 100 | 5 | 8 | 39 |

TABLE 1-continued

| | Catalyst (wt. % M2 wt. % Pt/Support) | M1 Precursor | M2 Precursor | Temp. (° C.) | Time (Hours) | Catalyst Amount (mg) | Glucaric Acid Yield (%) |
|---|---|---|---|---|---|---|---|
| [b]24 | [a]4% Pt/Titania NorPro ST 61120 | Pt(NO$_3$)$_2$ | None | 100 | 5 | 8 | 30 |
| [b]24 | 1.5% Pt 1.5% Au/Titania [Sud Chemie 02-10] | | Pt(NO$_3$)$_2$ | 100 | 5 | 8 | 55 |
| [b]25 | 4% Pt 4% Au/Titania NorPro ST 61120 | AuCl$_3$ | Pt(NO$_3$)$_2$ | 100 | 5 | 8 | 32 |

[a]These catalysts were calcined at 500° C. for 3 hours prior to reduction.
[b]These reactions were run under 500 psig of air, all other reactions in Table 1 were run under 75 psig of O$_2$.
Catalysts in examples 4-7, 11-12 were reduced at 200° C. under flowing 5 vol. % H$_2$ in N$_2$ for 3 hours.
Catalysts in examples 1-3, 8-10, 19-25 were reduced at 350° C. under flowing 5 vol. % H$_2$ in N$_2$ for 3 hours.
Commercial catalysts in examples 13-18 were screened directly.

Example 2

Glucaric Acid to Adipic Acid

Preparation of M1/Support Catalysts (M1=Ru, Rh, Pd, Pt)x 2 g of dried 5 μm Silica Cariact (Fuji Silysia) or 45 μm Titania NorPro ST 61120 (Saint-Gobain) was weighed into vials. Suitably concentrated M1 stock solutions (M1=Ru, Rh, Pd, Pt) were prepared from concentrated acidic stock solutions purchased from Heraeus (see Table 1). For each M1, multiple additions of the dilute M1 stock solution were added to the Support (Silica pore volume=0.7 mL/g, Titania NorPro=0.45 mL/g) until a total volume of 1.4 ml (Silica) or 0.9 mL (Titania) was reached. After each addition, the mixtures were agitated to impregnate the support. Post impregnation, the X wt. % M1/Support mixtures (X=2-5) were dried in a furnace at 120° C. for 12 hours.

Preparation of M1/M2/Support Catalysts (M2=Ru, Rh, Pd, Ir, Pt, Au, Mo)

7-12 mg of dried X wt. % M1/Support (M1=Ru, Rh, Pd Pt) (X=2-5) were dispensed into 8×12 arrays containing 1 mL glass vials. To select vials within the array, 3-8 μl (where the total addition volume was matched to equal to the pore volume of the dried X wt. % M1/Support catalysts weighed into the vial) of suitably concentrated M2 stock solutions were added (M2=Ru, Rh, Pd, Ir, Pt, Au (obtained from Heraeus), and Mo (obtained from Strem), see Table 1). Post M2 addition, the mixtures were agitated via a multi-tube vortexer to impregnate the supports. Post impregnation, the glass vial arrays of M1/M2/Support catalysts were dried in a furnace at 120° C. for 1 hour, followed by calcination at 500° C. for 3 hours. Upon cooling the arrays of catalysts were stored in a dessicator until used.

Preparation of M1/M2/Support Catalysts by Coimpregnation (M1/M2=Rh, Pd, Pt)

7-12 mg of silica support (Davisil 635 W.R.Grace & Co.) were dispensed into 8×12 arrays containing 1 mL glass vials. Supports were dried at 120° C. for 12 hours prior to use. To select vials within the array, 6-11 682 1 (where the total addition volume was matched to equal to the pore volume of the Support weighed into the vial) of suitably concentrated pre-mixed M1/M2 stock solutions were added (M1/M2 =Rh, Pd, Pt) (obtained from Heraeus), Post metal addition, the mixtures were agitated via a multi-tube vortexer to impregnate the supports. Post impregnation, the glass vial arrays of M1/M2/Support catalysts were dried in a furnace at 120° C. for 1 hour, followed by calcination at 500° C. for 3 hours. Upon cooling the arrays of catalysts were stored in a dessicator until used.

Glucaric Acid to Adipic Acid Reactions

The arrays of catalysts were transferred to 1 mL glass vials within a 96-well reactor insert (Symyx Solutions). Each vial within each array received a glass bead and 250 μL of 0.2 M Glucaric Acid (prepared from calcium glucarate) (Sigma-Adrich), 0.1 M HBr (examples 1-37; Sigma-Aldrich) or 0.2 M HBr (example 38; Sigma-Aldrich) in Acetic Acid (Sigma-Aldrich). Upon solution addition, the arrays of vials were covered with a Teflon pin-hole sheet, a silicone pin-hole mat and steel gas diffusion plate (Symyx Solutions). The reactor insert was placed in a pressure vessel pressurized and vented 3 times with nitrogen and 3 times with hydrogen before being pressurized with hydrogen to 710 psig, heated to 140 ° C. (examples 1-37) or 160° C. (example 38) and shaken for 3 hours. After 3 hours the reactors were cooled, vented and purged with nitrogen. 750 μl of water was then added to each vial. Following the water addition, the arrays were covered and shaken to ensure adequate mixing. Subsequently, the covered arrays were placed in a centrifuge to separate the catalyst particles. Each reaction samples was then diluted 2-fold with water to generate a sample for analysis by HPLC. The results are presented in Table 2.

TABLE 2

| | Catalyst (wt. % M2 wt. % M1/Support) | M1 Precursor | M2 Precursor | Catalyst Amount (mg) | Adipic Acid Yield (%) |
|---|---|---|---|---|---|
| 1 | 0.5% Pd 5% Rh/Silica 5 μm Cariact | Rh(NO$_3$)$_3$ | Pd(NO$_3$)$_2$ | 8 | 51 |
| 2 | 0.5% Pd 5% Rh/Silica 5 μm Cariact | Rh(NO$_3$)$_3$ | Pd(NO$_3$)$_2$ | 8 | 53 |
| 3 | 0.5% Ru 5% Pd/Silica 5 μm Cariact | Pd(NO$_3$)$_2$ | [a]Ru(NO)(NO$_3$)$_x$(OH)$_y$ | 8 | 74 |
| 4 | 0.5% Ru 5% Pd/Silica 5 μm Cariact | Pd(NO$_3$)$_2$ | [a]Ru(NO)(NO$_3$)$_x$(OH)$_y$ | 8 | 77 |
| 5 | 0.5% Ru 5% Rh/Silica 5 μm Cariact | Rh(NO$_3$)$_3$ | [a]Ru(NO)(NO$_3$)$_x$(OH)$_y$ | 10 | 50 |
| 6 | 0.5% Ru 5% Rh/Silica 5 μm Cariact | Rh(NO$_3$)$_3$ | [a]Ru(NO)(NO$_3$)$_x$(OH)$_y$ | 8 | 57 |
| 7 | 1% Ir 5% Rh/Silica 5 μm Cariact | Rh(NO$_3$)$_3$ | H$_2$IrCl$_6$•H$_2$0 | 8 | 53 |
| 8 | 2.5% Mo 5% Pd/Silica 5 μm Cariact | Pd(NO$_3$)$_2$ | (NH$_4$)$_6$Mo$_7$O$_{24}$ | 8 | 53 |
| 9 | 2.5% Pd 5% Rh/Silica 5 μm Cariact | Rh(NO$_3$)$_3$ | Pd(NO$_3$)$_2$ | 8 | 50 |
| 10 | 2.5% Pd 5% Rh/Silica 5 μm Cariact | Rh(NO$_3$)$_3$ | Pd(NO$_3$)$_2$ | 13 | 50 |
| 11 | 2.5% Ru 5% Pd/Silica 5 μm Cariact | Pd(NO$_3$)$_2$ | [a]Ru(NO)(NO$_3$)$_x$(OH)$_y$ | 8 | 63 |
| 12 | 2.5% Ru 5% Pd/Silica 5 μm Cariact | Pd(NO$_3$)$_2$ | [a]Ru(NO)(NO$_3$)$_x$(OH)$_y$ | 8 | 63 |
| 13 | 2.5% Ru 5% Rh/Silica 5 μm Cariact | Rh(NO$_3$)$_3$ | [a]Ru(NO)(NO$_3$)$_x$(OH)$_y$ | 11 | 51 |

TABLE 2-continued

| Catalyst (wt. % M2 wt. % M1/Support) | M1 Precursor | M2 Precursor | Catalyst Amount (mg) | Adipic Acid Yield (%) |
|---|---|---|---|---|
| 14 2.5% Ru 5% Rh/Silica 5 μm Cariact | Rh(NO$_3$)$_3$ | [a]Ru(NO)(NO$_3$)$_x$(OH)$_y$ | 8 | 54 |
| 15 5% Ir 5% Rh/Silica 5 μm Cariact | Rh(NO$_3$)$_3$ | H$_2$IrCl$_6$•H$_2$O | 8 | 52 |
| 16 5% Pt 5% Pd/Silica 5 μm Cariact | Pd(NO$_3$)$_2$ | Pt(NO$_3$)$_2$ | 8 | 54 |
| 17 [b]5% Rh/Silica 5 μm Cariact | Rh(NO$_3$)$_3$ | None | 8 | 49 |
| 18 [b]5% Pd/Silica 5 μm Cariact | Pd(NO$_3$)$_2$ | None | 8 | 47 |
| [d]19 [b]5% Pt/Silica 5 μm Cariact | Pt(NO$_3$)$_2$ | None | 8 | 69 |
| 20 0.5% Au 5% Rh/Silica 5 μm Cariact | Rh(NO$_3$)$_3$ | AuCl$_3$ | 9 | 48 |
| 21 0.5% Au 5% Rh/Silica 5 μm Cariact | Rh(NO$_3$)$_3$ | AuCl$_3$ | 14 | 50 |
| 22 2% Pd 2% Rh/Titania NorPro ST 61120 | Rh(NO$_3$)$_3$ | Pd(NO$_3$)$_2$ | 8 | 47 |
| 23 2% Pd 4% Pt/Titania NorPro ST 61120 | Pt(NO$_3$)$_2$ | Pd(NO$_3$)$_2$ | 7 | 38 |
| 24 4% Pt 2% Ru/Titania NorPro ST 61120 | [a]Ru(NO)(NO$_3$)$_x$(OH)$_y$ | Pt(NO$_3$)$_2$ | 9 | 46 |
| 25 4% Pt 2% Rh/Titania NorPro ST 61120 | Rh(NO$_3$)$_3$ | Pt(NO$_3$)$_2$ | 8 | 60 |
| 26 4% Pt 2% Pd/Titania NorPro ST 61120 | Pd(NO$_3$)$_2$ | Pt(NO$_3$)$_2$ | 7 | 39 |
| 27 2% Ru 2% Pd/Titania NorPro ST61120 | Pd(NO$_3$)$_2$ | [a]Ru(NO)(NO$_3$)$_x$(OH)$_y$ | 12 | 22 |
| 28 2% Ru 4% Pt/Titania NorPro ST 61120 | Pt(NO$_3$)$_2$ | [a]Ru(NO)(NO$_3$)$_x$(OH)$_y$ | 8 | 38 |
| 29 2% Rh 2% Pd/Titania NorPro ST61120 | Pd(NO$_3$)$_2$ | Rh(NO$_3$)$_3$ | 7 | 46 |
| 30 2% Rh 4% Pt/Titania NorPro ST 61120 | Pt(NO$_3$)$_2$ | Rh(NO$_3$)$_3$ | 9 | 52 |
| 31 [c]1.6% Rh 1.6% Pd/Silica Davisil 635 | Pd(NO$_3$)$_2$ | Rh(NO$_3$)$_3$ | 8 | 51 |
| 32 [c]1.6% Rh 3.0% Pt/Silica Davisil 635 | Pt(NO$_3$)$_2$ | Rh(NO$_3$)$_3$ | 8 | 61 |
| 33 [c]0.3% Rh 5.4% Pt/Silica Davisil 635 | Pt(NO$_3$)$_2$ | Rh(NO$_3$)$_3$ | 8 | 47 |
| 34 [b]3.2% Pd/Silica Davisil 635 | Pd(NO$_3$)$_2$ | none | 8 | 46 |
| 35 [b]6.0% Pt/Silica Davisil 635 | Pt(NO$_3$)$_2$ | none | 8 | 35 |
| 36 [b]3.2% Rh/Silica Davisil 635 | Rh(NO$_3$)$_3$ | none | 8 | 30 |
| 37 [c]0.6% Pt 2.9% Pt/Silica Davisil 635 | Pd(NO$_3$)$_2$ | Pt(NO$_3$)$_2$ | 8 | 45 |
| [e]38 [c]1.65% Rh 4.7% Pt/Silica Davisil 635 | Pt(NO$_3$)$_2$ | Rh(NO$_3$)$_3$ | 8 | 89 |

[a]Where x + y = 3
[b]Where no M2 was used, the M1/Support catalyst was calcined at 500° C. for 3 hours prior to use
[c]Prepared by coimpregnation
[d]This reaction was run for 6 hours
[e]This reaction was conducted at 160° C.

What is claimed is:

1. A process for preparing glucaric acid or lactone thereof, the process comprising:
reacting glucose with oxygen in the presence of a heterogeneous oxidation catalyst comprising a metal selected from the group consisting of Pd, Pt, and a combination thereof to convert at least a portion of the glucose to glucaric acid or lactone thereof, wherein the pH of the reaction mixture is less than 7 and the reaction is conducted in the substantial absence of added base, and wherein at least about 50% of the glucose is converted to glucaric acid or lactone thereof.

2. The process as set forth in claim 1 wherein at least about 60% of the glucose is converted to glucaric acid or lactone thereof.

3. The process as set forth in claim 1 wherein at least about 50% of the glucose is converted to glucaric acid.

4. The process as set forth in claim 1 wherein at least a portion of the glucose is converted to a glucarolactone.

5. The process as set forth in claim 1 wherein at least a portion of the glucose is solubilized with a weak carboxylic acid.

6. The process as set forth in claim 5 wherein the weak carboxylic acid is acetic acid.

7. The process as set forth in claim 1 wherein the heterogeneous oxidation catalyst comprises Pt.

8. The process as set forth in claim 7 wherein the heterogeneous oxidation catalyst further comprises Au.

9. The process as set forth in claim 1 wherein the heterogeneous oxidation catalyst comprises a catalyst support selected from the group consisting of carbon, alumina, silica, titania, zirconia, and zeolite.

10. The process as set forth in claim 9 wherein the catalyst support comprises carbon.

11. The process as set forth in claim 10 wherein the catalyst support comprises carbon black.

12. The process as set forth in claim 1 wherein the reaction mixture is maintained at a temperature of at least about 60° C.

13. The process as set forth in claim 1 wherein the reaction mixture is maintained at a temperature from about 60° C. to about 150° C.

14. The process as set forth in claim 1 wherein the reaction is conducted under a partial pressure of oxygen that is at least about 60 psia (414 kPa).

15. The process as set forth in claim 1 wherein the reaction is conducted under a partial pressure of oxygen in the range of from about 15 psia (104 kPa) to about 2000 psia (13790 kPa).

16. The process as set forth in claim 1 wherein the glucose is obtained from a carbohydrate source.

17. The process as set forth in claim 1 wherein the oxygen is supplied to the reaction as air, oxygen-enriched air, oxygen alone, or oxygen with one or more other constituents substantially inert to the reaction.

18. The process as set forth in claim 1 wherein the reaction mixture is essentially free of nitrogen as an active reaction constituent.

19. The process as set forth in claim 1 wherein the metal selected from the group consisting of Pd, Pt, and a combination thereof constitutes from about 1% to about 8% of the total weight of the heterogeneous oxidation catalyst.

20. A process for preparing adipic acid, the process comprising:
preparing glucaric acid or lactone thereof according to the process as set forth in claim 1; and
reacting, in the presence of a hydrodeoxygenation catalyst, a halogen source and hydrogen, at least a portion of the glucaric acid or lactone thereof, to convert at least a portion of the glucaric acid or lactone thereof to adipic acid.

21. The process as set forth in claim 7 wherein the heterogeneous oxidation catalyst comprises a catalyst support selected from the group consisting of carbon, alumina, silica, titania, zirconia, and zeolite.

22. The process as set forth in claim 21 wherein the catalyst support comprises carbon.

23. The process as set forth in claim 22 wherein the catalyst support comprises carbon black.

24. The process as set forth in claim 1 wherein the heterogeneous oxidation catalyst further comprises a second metal besides Pd and/or Pt.

25. The process as set forth in claim 24 wherein the molar ratio of the Pd and/or Pt to the second metal is from about 10:1 to about 1:1.

26. The process as set forth in claim 7 wherein at least about a portion of the glucose is converted to glucaric acid, the reaction mixture is maintained at a temperature from about 80° C. to about 120° C., and the reaction is conducted under a partial pressure of oxygen in the range of from about 15 psia (104 kPa) to about 2000 psia (13790 kPa).

27. The process as set forth in claim 26 wherein the heterogeneous oxidation catalyst comprises a catalyst support selected from the group consisting of carbon, alumina, silica, titania, zirconia, and zeolite.

28. The process as set forth in claim 27 wherein the catalyst support comprises carbon.

29. The process as set forth in claim 28 wherein the catalyst support comprises carbon black.

30. The process as set forth in claim 27 wherein the heterogeneous oxidation catalyst further comprises a second metal besides Pd and/or Pt and the molar ratio of Pt to the second metal is from about 10:1 to about 1:1.

31. The process as set forth in claim 7 wherein at least about 60% of the glucose is converted to glucaric acid or lactone thereof.

32. The process as set forth in claim 7 wherein at least about 50% of the glucose is converted to glucaric acid.

33. The process as set forth in claim 8 wherein at least about 60% of the glucose is converted to glucaric acid or lactone thereof.

34. The process as set forth in claim 8 wherein at least about 50% of the glucose is converted to glucaric acid.

35. The process as set forth in claim 1 wherein the heterogeneous oxidation catalyst comprises Pd.

36. The process as set forth in claim 35 wherein at least about 60% of the glucose is converted to glucaric acid or lactone thereof.

37. The process as set forth in claim 35 wherein at least about 50% of the glucose is converted to glucaric acid.

38. The process as set forth in claim 7 wherein the pH of the reaction mixture is less than 6.

39. The process as set forth in claim 8 wherein the pH of the reaction mixture is less than 6.

* * * * *